United States Patent [19]

Gum

[11] Patent Number: 4,801,447
[45] Date of Patent: Jan. 31, 1989

[54] WATER-IN-VOLATILE SILICONE EMULSIFIER CONCENTRATES, WATER-IN-VOLATILE SILICONE EMULSIONS THAT ARE USEFUL IN PERSONAL-CARE FORMULATIONS AND METHODS OF MAKING SAME

[75] Inventor: Mary L. Gum, Granite Springs, N.Y.

[73] Assignee: Union Carbide Corporation, Danbury, Conn.

[21] Appl. No.: 808,839

[22] Filed: Dec. 13, 1985

Related U.S. Application Data

[62] Division of Ser. No. 580,320, Feb. 22, 1984, abandoned.

[51] Int. Cl.$^4$ .......................... A61K 7/06; A61K 7/32; A61K 7/38; A61K 7/48
[52] U.S. Cl. ........................................ 424/68; 424/70; 514/844; 514/846; 514/847; 514/941
[58] Field of Search ............... 514/941, 844, 846, 847; 424/68, 70

[56] References Cited

U.S. PATENT DOCUMENTS

| | | | |
|---|---|---|---|
| 3,234,252 | 2/1966 | Pater ........................... | 252/49.6 X |
| 3,472,840 | 10/1969 | Stone et al. ........................ | 260/231 |
| 3,489,690 | 1/1970 | Lachampt et al. ................... | 252/308 |
| 3,641,239 | 2/1972 | Mohrlok ............................. | 424/64 |
| 4,122,029 | 10/1978 | Gee et al. ........................... | 252/309 |
| 4,311,695 | 1/1982 | Starch ................................ | 424/184 |
| 4,342,742 | 8/1982 | Sebag et al. ........................ | 424/70 |
| 4,344,763 | 8/1982 | Tolgyesi et al. ..................... | 424/70 |
| 4,374,825 | 2/1983 | Bolich, Jr. et al. .................. | 424/70 |
| 4,387,090 | 6/1983 | Bolich, Jr. .......................... | 424/70 |
| 4,421,769 | 12/1983 | Dixon et al. ........................ | 424/184 |

FOREIGN PATENT DOCUMENTS

| | | | |
|---|---|---|---|
| 0035899 | 9/1981 | European Pat. Off. .............. | 424/70 |
| 2033191 | 12/1970 | France ............................... | 424/184 |
| 0057337 | 5/1977 | Japan ................................. | 424/70 |
| 0066506 | 5/1980 | Japan ................................. | 424/184 |
| 0092808 | 7/1981 | Japan ................................. | 424/70 |
| 1158139 | 10/1966 | United Kingdom ............... | 424/184 |
| 1221156 | 7/1969 | United Kingdom ............... | 424/70 |
| 2058103 | 4/1981 | United Kingdom ............... | 424/70 |
| 2102288A | 6/1982 | United Kingdom ............... | 424/70 |

OTHER PUBLICATIONS

Disapio and Starch, Cosmetics & Toiletries, vol. 96, pp. 55–57.
Commercial Product Information "Dow Corning Q2–3225C Formulation Aid".

*Primary Examiner*—Dale R. Ore
*Attorney, Agent, or Firm*—Steven H. Flynn

[57] ABSTRACT

Water-in-volatile silicone emulsifier concentrates containing 2 to 30 wt. % water in the internal phase, 40 to 90 wt. % of a volatile cyclic silicone liquid such as the octamethylsiloxane cyclic tetramer, decamethylsiloxane cyclic pentamer or the dodecamethylsiloxane cyclic hexamer and 5 to 40 wt. % of a polyoxyalkylene substituted silicone containing per molecule 5 to 100 dialkylsiloxy units, two trialkylsiloxy end blocking units and 1 to 16 polyoxyalkylene substituted alkylsiloxy units of the average formula:

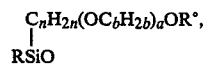

$$\begin{array}{c} C_nH_{2n}(OC_bH_{2b})_aOR^\circ, \\ | \\ RSiO \end{array}$$

in which R is an alkyl group having 1 to 4 carbon atoms and R can individually be the same or different, wherein R° is a terminal group selected from the class consisting of hydrogen, alkyl, aryl, aralkyl and acyl radicals, n is an integer of 2 to 8, a is a number of 5 to 20 and b is 2 or 3. Said emulsifier concentrates are highly useful in preparing water-in-silicone personal-care emulsions by simply mixing same with desired personal-care components soluble therein followed by mixing with water in which water soluble personal-care components may be mixed. The personal-care components include the well known materials such as emollients, film formers, sun screen agents, moisture barriers, anti-perspirants and the like. Processes are also described for preparing the water-in-silicone emulsifier concentrates and emulsions mentioned above.

21 Claims, 1 Drawing Sheet

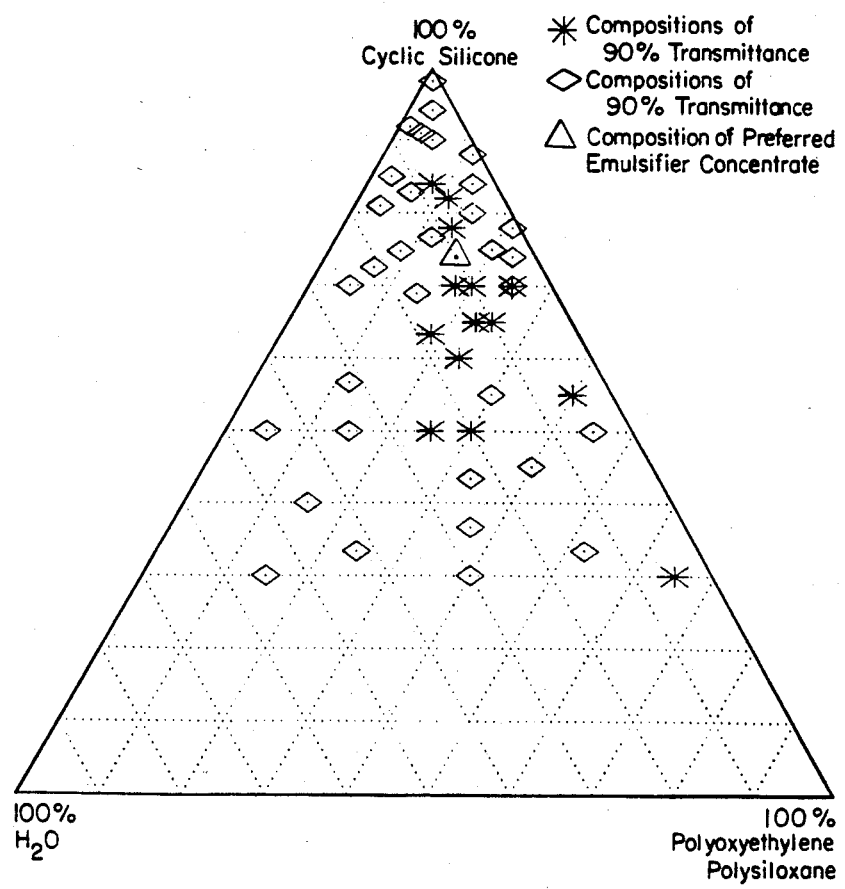

WATER-IN-VOLATILE SILICONE EMULSIFIER CONCENTRATES, WATER-IN-VOLATILE SILICONE EMULSIONS THAT ARE USEFUL IN PERSONAL-CARE FORMULATIONS AND METHODS OF MAKING SAME

This application is a division of prior U.S. application Ser. No. 580,320, filing date 2/22/84, now abandoned.

BACKGROUND OF THE INVENTION

1. Field of the Invention

This invention relates to novel water-in-volatile silicone emulsifier concentrates and to personal-care emulsion compositions of the water-in-oil type, i.e., water-in-volatile silicone. More specifically, this invention also relates to dry feeling personal-care lotions, creams, hair dressings, and other compositions for application to the human skin or hair for the purposes of conditioning the skin, e.g., moisturizing the skin, providing anti-perspirant protection, providing protection from the sun, or for conditioning the hair to make it more manageable, to improve its wet and dry combability and reduce "fly away" tendency of the hair. In one aspect, the novel emulsifier concentrates contain water-in-volatile cyclic silicone and an emulsifier comprising trimethylsiloxy end-blocked polydiorganosiloxanes having one or more pendant polyoxyalkylene chain of a molecular weight of less than 1000 bonded to silicon through an alkylene group. The personal-care emulsions are made by mixing the emulsifier concentrate, which may or may not contain personal-care components soluble therein, with water up to 90 wt. % of the total composition wherein said water may or may not contain water soluble personal-care components.

2. Description of the Prior Art

Water-in-volatile silicone personal-care emulsion compositions are disclosed in British Pat. No. 1,158,139. These water-in-volatile silicone emulsions in which the only emulsifier is an organic emulsifier are lacking in stability, especially when the aqueous phase contains a dissolved solute. U.S. Pat. No. 3,489,690 describes certain water-in-oil emulsions using certain polyoxyalkylene alcohols as emulsifiers and a silicone oil in the oil phase. These emulsions can also be expected to be lacking in suitable stability, particularly if the aqueous phase contains a dissolved solute. British Pat. No. 1,221,156 discloses water-in-oil emulsions for use as ointment bases for skin protection and skin care agents and which contain organosiloxane-oxyalkylene block copolymers as the external phase containing from 50 to 85% water as the internal phase. However, this patent does not disclose or suggest the use of a volatile silicone liquid as the oil phase in which water is dispersed as the internal phase by means of a polyoxyalkylene substituted block copolymer as described and claimed herein.

U.S. Pat. No. 3,234,252 discloses aqueous lubricating compositions in the nature of emulsions containing siloxane-polyoxyalkylene copolymers as additives. It has been reported (U.S. Pat. No. 4,122,029) that when one attempts to prepare water in low viscosity polydimethylsiloxane emulsions using only a siloxane polyoxyalkylene copolymer as an emulsifier, suitable stable emulsions are not obtained.

U.S. Pat. No. 4,122,029 discloses that emulsion compositions comprising water-in-volatile polydimethylsiloxane fluid can be prepared by using mixtures of certain organic surfactants and certain polydiorganosiloxane-polyoxyalkylene copolymers as the mixture of emulsifying agents. According to the disclosure in '029, the presence of an organic surfactant is necessary and the molecular weight of the oxyalkylene chains in the polysiloxane-polyoxyalkylene copolymers must be at least 1000. However, molecular weights of the polyoxyalkylene chains utilized in '029 result in relatively high viscosity, relatively high molecular weight, materials and emulsions. In terms of performance in personal-care or cosmetic applications, the materials disclosed in this patent are very dull and waxy in appearance which is probably due to the high molecular weight of the polyalkylene chains which approach wax-like characteristics.

U.S. Pat. No. 4,311,695 discloses personal-care emulsions of the water-in-oil type in which a water-alcohol solution is described as being dispersed within a volatile silicone liquid (or paraffinic hydrocarbon liquid) utilizing a polydiorganosiloxane-polyoxyalkylene copolymer containing polyoxyalkylene chains having an average molecular weight of at least 1000. These compositions also tend to have a dull and wax-like appearance presumably because of the presence of relatively long polyoxyalkylene chains.

DiSapio and Starch in *Cosmetics & Toiletries*, Vol. 96, pp. 55-57, disclose personal-care products which appear to be substantially the same as the emulsions described in the above-mentioned U.S. Pat. Nos. 4,311,695 and 4,122,029.

U.S. Pat. No. 4,374,825 discloses oil-in-water emulsions containing a volatile liquid hydrocarbon or silicone, a non-ionic water soluble thickener of an organic nature and a cationic hair conditioner agent comprising quaternary ammonium salts also of an organic nature. U.S. Pat. No. 4,387,090 refers to a hair conditioner composition containing a volatile silicone agent and a hydrophobic polymeric thickening agent of an organic nature. There is no mention in these patents of the utilization of a polyoxyalkylene substituted polysiloxane as an emulsifier or dispersant.

British patent application No. 2102288A discloses a hair conditioning composition which contains volatile silicone and a quaternary nitrogen-containing agent of a polymeric or non-polymeric structure, a long chain fatty alcohol and a tertiary amidoamine. This disclosure however does not disclose water-in-oil emulsions and also fails to disclose the employment of a polyoxyalkylene substituted polysiloxane in which the polyoxyalkylene chains have a molecular weight of less than 1000.

None of the above-identified references discloses or teaches this invention, that is, they do not disclose, teach or suggest any water-in-silicone emulsifier concentrate containing a volatile silicone liquid, water and a polyoxyalkylene substituted polysiloxane in which each polyoxyalkylene chain has a molecular weight of less than 1000 or water-in-silicone emulsions containing personal-care components made from said concentrates.

The cosmetic industry has a high level of interest in emulsions containing volatile silicones, especially for hair care products. The rationale for this approach has been to reduce the amount of oily-type materials in hair conditioners which give rise to the "greasies", but at the same time provide good wet and dry combability and reduced fly away. Volatile silicones remain on the hair for 24 hours or less depending on a number of factors, so that as the hair is receiving increasing amounts of oil from the scalp the amount of volatile silicone on the hair is decreasing.

SUMMARY OF THE INVENTION

This invention relates to water-in-silicone emulsifier concentrates which are highly useful for preparing stable water-in-volatile silicone emulsions containing very large amounts of water, e.g. as high as 98%. The novel emulsifier concentrates contain major amounts of volatile silicone and minor amounts of water and polyoxyalkylene substituted polysiloxane wherein each polyoxyalkylene chain has a molecular weight of less than 1000. The emulsifier concentrate and the water-in-volatile silicone emulsions prepared therefrom have good stability at normal room temperatures and even as low as 4° C. and as high as 50° C. Those compositions containing 75% or less water are also stable through one or more freeze/thaw cycles. The polyoxyalkylene polysiloxane copolymer does not impart a dull or waxy appearance to the emulsion such as results when polyoxyalkylene polysiloxane copolymers having molecular weights in excess of 1000 are used in the emulsions.

Personal-care components of the known types are also included in the personal-care water-in-silicone emulsions of this invention. Such known personal-care products are in many cases oil soluble, i.e. soluble in the volatile silicone phase and can be present therein in the novel compositions. In other cases the personal-care component is water soluble in which case it is present in the water phase of the novel compositions.

The novel compositions are of relatively low viscosity and can be easily prepared, handled and packaged and used. The novel compositions furthermore provide a much superior appearance and feel for cosmetic applications and do not possess the very dull, waxy characteristics of prior art systems wherein polyoxyalkylene chains of molecular weight greater than 1000 are essential.

DESCRIPTION OF THE INVENTION

The water-in-volatile silicone emulsifier concentrates of this invention contain a minimum of three components including: (a) water in the internal phase, (b) a volatile cyclic silicone liquid in the external phase, and (c) a polyoxyalkylene substituted silicone primarily at the interface but also may be present in the aqueous and silicone phases. The volatile cyclic silicone has a normal boiling point of less than 260° C., preferably less than 250° C. Suitable cyclic silicone liquids are those having the average formula:

$$[R_2SiO]_x$$

wherein R is an alkyl group having 1 to 4 carbon atoms such as methyl where R can individually be the same or different and x is an integer of 4 to 6. These materials are readily available. The especially preferred cyclic silicone liquids are octamethyltetrasiloxane, $[Me_2SiO]_4$, decamethylpentasiloxane, $[Me_2SiO]_5$, or dodecamethylhexasiloxane $[Me_2SiO]_6$, or mixtures thereof where Me is $CH_3$.

The polyoxyalkylene substituted silicone surfactant used in the novel compositions of this invention can be represented by the average formula: $MD_yD°_zM$, wherein M is a trialkylsiloxy unit having the average formula, $R_3SiO_{0.5}$, where R can individually be the same or different such as trimethylsiloxy, $Me_3SiO_{0.5}$, or dimethylethylsiloxy, $Me_2(C_2H_5)SiO_{0.5}$, D is a dialkylsiloxy unit of the formula, $R_2SiO$, D° is a polyoxyalkylene substituted alkylsiloxy unit of the average formula:

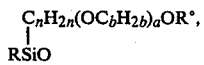

wherein R is an alkyl group having 1 to 4 carbon atoms and wherein R° is a terminal group selected from the class consisting of hydrogen, alkyl, aryl, aralkyl and acyl radicals, n is an integer of 2 to 8, preferably 3 or 4, a is a number of 3 to 20, preferably 5 to 12, b is 2 or 3, y is a number of 5 to 100, preferably 15 to 30, z is a number of 1 to 16. Preferably, the polyoxyalkylene chain, $(OC_bH_{2b})_a$, contains an average 50 wt. % or more of oxyethylene units and most preferably contains 100% oxyethylene units. Typical polyoxyalkylene substituted alkoxy units include:

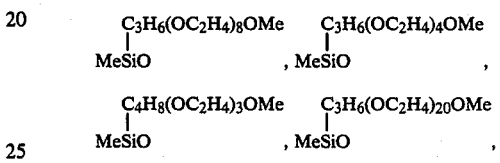

and the like.

The proportions of the above-mentioned components of the emulsifier concentrate are not narrowly critical and can be varied within relatively wide ranges. The amount of water for example can vary from 2 to 30 wt. %, preferably between 5 to 20 wt. % and most preferably 8 to 20 wt. %. The amount of volatile cyclic silicone liquid can be varied from 45 to 90 wt. %, preferably 50 to 85 wt. % and most preferably in the range from 60 to 80 wt. %. The amount of polyoxyalkylene substituted silicone as defined above is present in the novel emulsifier concentrates in the amounts of 5 to 50 wt. %, preferably 10 to 30 wt. %, most preferably 12 to 28 wt. %. These percentages are based on the total weight of water, volatile cyclic silicone and polyoxyalkylene substituted silicone in the emulsifier concentrate composition.

The water-in-volatile silicone emulsifier concentrates of this invention are easily prepared by mixing cyclic silicone, water and polyoxyalkylene substituted silicone as described above and there results a dispersion which has good stability. In the absence of water however, the stability of the dispersions is impaired. Thus, the addition of water improves the stability of the dispersion dramatically. The emulsifier concentrate is prepared by premixing the water, volatile silicone and the polyoxyalkylene substituted polysiloxane using any suitable method of mixing such as a bench top jar mill. The order of addition of components has not been found to be critical, for example, various orders of addition have been utilized including first mixing water and the polyoxyalkylene polysiloxane followed by mixing in the volatile silicone. Alternatively, either the water can be added to the polyoxyalkylene polysiloxane followed by addition of the cyclic silicone followed by mixing, or the cyclic silicone can be added to the polyoxyalkylene polysiloxane and mixed therein followed by addition of water with mixing. Another way is to add the cyclic silicone to the polyoxyalkylene polysiloxane followed by adding water and then mixing, or the cyclic silicone can be added to the water with or without mixing followed by addition of the polyoxyalkylene polysiloxane with mixing. The materials can be added in small proportions with mixing over a period of time, for example, all the water can be added to all of the polyoxyalkylene polysiloxane followed by mixing and then addition of at four intervals one quarter of the amount of the cyclic silicone with mixing. Likewise, all the cyclic silicone can be added to the polyoxyalkylene polysiloxane with mixing followed by four separate additions of one quarter of the amount of water with mixing at each addition. Furthermore, all the cyclic silicone can be added to all of the water followed by four sequential additions each of one quarter of the amount of polyoxyalkylene polysiloxane. A study was carried out to determine the regions of clarity on a phase diagram for the three-component emulsifier concentrate system. Each mixture was prepared by first mixing the appropriate amounts of polyoxyalkylene polysiloxane, namely,

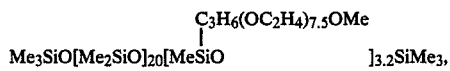

(hereinafter called the preferred polyoxyalkylene polysiloxane), and water on a bench jar mill with subsequent addition of the appropriate amounts of cyclic silicone followed by further mixing. The drawing depicts a ternary diagram of the three-component emulsifier concentrate compositions. Each mixture is identified by a diamond or an asterisk on the drawing except that the most preferred emulsifier concentrate is designated by a triangle. The asterisks designate emulsifier concentrate compositions which had a clarity of 90% or more transmittance as measured by a Brinkman colorimeter equipped with a fiber optic light guide and Pyrex flow-through probe. The compositions designated with diamonds showed less than 90% transmittance which was chosen as a level such that compositions represented by diamonds were still useful emulsifier concentrates albeit having less clarity and being less desired than the compositions represented by asterisks. As can be seen in the figure, there is a region of high clarity extending from the silicone apex down toward the 50% silicone composition line.

The preferred emulsifier concentrate composition (triangle) is located at the upper portions of the region of high clarity. Increasing levels of polyoxyalkylene polysiloxane tend to cause rapid viscosity build-up, particularly when making high internal phase emulsions, that is, high water emulsions. In cases of extremely high water content and high levels of polyoxyalkylene polysiloxane, gel-like structures are formed.

The most preferred emulsifier concentrates of this invention produce stable water-in-volatile silicone emulsions under shear conditions provided by a paddle stirrer using 75% water as the internal phase. The novel water-in-volatile silicone emulsions can be prepared in any number of ways. For example, by the slow addition of water through a dropping funnel into a three-necked flask equipped with a stirring blade and containing a dispersion of the polyoxyalkylene copolymer in the cyclic silicone. Stable emulsions have been prepared by this method at a water content of about 74 to 75% as the internal phase and about 20 to 21% of the cyclic silicone as the external phase and approximately 4 to 4.5% of the polyoxyalkylene polysiloxane. A low level of shear is sufficient for emulsion formation and this indicates that the emulsions are readily formed.

Typical commercial hair conditioner formulations contain about 90% water. The conventional hair conditioners, however, are oil-in-water emulsions so that obtaining a 90% water system presents no problems for these types of products because water is the external phase. However, with water-in-oil emulsions, a very high internal phase ratio is necessary in a 90% water emulsion. As one increases the internal phase, i.e. water, to external phase, i.e. cyclic silicone, ratio the viscosity of the emulsion increases. Higher shear mixing is needed for the more viscous emulsions. For example, a Hobart TM mixer Model N50 provides higher shear and was used in preparing the 90% water emulsions pursuant to this invention.

Stable 90% water-in-oil emulsions can be prepared utilizing the proper temperature and rate of water addition to the emulsifier concentrates described above. If water is added too quickly, the proper build of viscosity might not be obtained and, if added too slowly, the emulsion might become extremely viscous. After prolonged stirring the emulsion droplets become so finely divided that there is insufficient emulsifier, i.e. polyoxyalkylene polysiloxane, in the system to stabilize the water droplets. Best results generally were obtained at temperatures of about 20° C.; however, there is a relationship between the cloud point of the polyoxyalkylane and the required temperature of mixing water with the emulsifier concentrate. Higher cloud point polyoxyalkylene polysiloxanes can result in inversion of the emulsion during or after its making. However, this effect is overcome by using higher mixing temperatures, e.g., 40° C. for preparing the emulsion or by adding salt (NaCl) in amounts up to 2 wt. % or more, e.g., 0.2 to 2 wt. % based on the weight of the emulsion, or by doing both.

Emulsions of this invention having a high internal phase (water) are typically prepared by weighing 30 wt. parts of the emulsifier concentrate such as the preferred emulsifier concentrate described above and given in Example 1 hereinbelow into the bowl of the Hobart TM mixer identified above. While mixing on the #1 setting of the Hobart TM mixer, water is added at the rate of about 8.3 wt. parts per minute until a total of 270 wt. parts of water has been added over a period of 32.5 minutes. The temperature of the mixture in the Hobart TM bowl is maintained at 40° C. by a heating mantle having a Variac TM control. After water addition has been completed, the heating mantle is turned off and the finished emulsion is post-mixed while cooling for 10 minutes. The range of water addition rates is believed not to be critical, e.g. up to 60 wt. parts per minute for a 30 wt. part quantity of emulsifier concentrate, i.e. a 270 wt. parts quantity of water is satisfactory. For the preparation of larger batches, the rate of water addition can probably be increased proportionately. The viscosity, of course, should be observed carefully to make sure the water is being properly incorporated into the emulsions.

It is not necessary to first make an emulsifier concentrate and then make the emulsion from the concentrate. High water-in-volatile silicone emulsions, e.g. 90% water-in-volatile silicone emulsions, can be made by adding water directly to a stirred dispersion of polyoxyalkylene polysiloxane in cyclic silicone in the respective appropriate amounts. A preferred concentration of the preferred polyoxyalkylene polysiloxane in a preferred finished emulsion of this invention is about 1.76% with about 90 wt. % water in about 8.23 wt. % cyclic silicone. It was found that for this particular system keeping the water at 90 wt. % the concentration of the preferred polyoxyalkylene polysiloxane when varied down to 0.9% at 20° C. produced stable emulsions having lower viscosities. When the amount of the preferred polyoxyalkylene polysiloxane was increased to 5%, the emulsion could not incorporate 90 wt. % water at 20° C. and the water level would have to be reduced with a proportionate increase in cyclic silicone content in order to provide a more stable emulsion. Further tests were made of the 90 wt. % water in cyclic silicone emulsions using the above-identified preferred polyoxyalkylene polysiloxane. These tests were performed at 50° C. and −20° C. Table 1 below describes the temperature at which each of the four emulsions tested was prepared, emulsions #1, #2 and #4 being made from the preferred polyoxyalkylene polysiloxane. Emulsions #2 and #4 contain 0.2 wt. % sodium chloride. In addition, emulsion #3 was prepared in which the commercial product Q2-3225C made by Dow Corning, believed to have been made pursuant to U.S. Pat. Nos. 4,122,029 and 4,311,695, was substituted for the emulsifier concentrate. The amounts of the respective preferred polyoxyalkylene polysiloxane emulsifiers was the same at which 1.76%. Emulsions #1, #2 and #4 also contained 8.23% of the dimethylsiloxane cyclic tetramer and, of course, 90 wt. % of water. At 50° C. all of the emulsions passed the 30 day stability tests and none of them passed the −20° C. stability tests, the freeze/thaw stability. The failure to pass the freeze/thaw testing is not surprising because of the extremely high level of water as the internal phase. If the amount of water is reduced from 90 wt. % to 75 wt. % in the emulsion, then the emulsions made with the preferred polyoxyalkylene emulsifier pass at least two freeze/thaw cycles.

TABLE 1

| Emulsion Number | Prep. Temp. °C. | Aqueous Phase | 50° C. Stability 30 days |
|---|---|---|---|
| 1 | 28 | H₂O | Pass |
| 2 | 28 | 0.2% NaCl | Pass |
| 3* | 20 | 0.2% NaCl | Pass |
| 4 | 40 | 0.2% NaCl | Pass |

*Comparative example

Standard hair testing protocols were used on 2 gram hair tresses of virgin brown hair for measuring wet and dry combability and fly away. The maximum combability value is 10 and the fly away is measured by the width of the hair tress after 10 rapid combings. The hair conditioner being tested is applied in the amount of 1 ml to a freshly shampooed hair tress. The hair conditioners tested were 90% water in octamethyltetrasiloxane cyclic tetramer made from the preferred emulsifier concentrate which was made pursuant to Example 1 present hereinbelow from 10 wt. parts water, 15.88 wt. parts of the preferred polyoxyalkylene siloxane and 74.12 wt. parts of the cyclic tetramer of dimethyl siloxane. In test #1 a control of water only was used. In tests #2–6 the 90% water-in-cyclic silicone tetramer emulsion was used. In tests #3 and #5 respectively, 0.5% and 1% of quaternary ammonium hydroxyethyl cellulose derivative (Polymer JR ™ sold by Union Carbide Corporation) was added to the emulsion and in tests #4 and #6 respectively, 0.5 wt. % and 1 wt. % of a similar but different quaternary nitrogen hydroxyethyl cellulose derivative (made and sold as Polymer LR ™ by Union Carbide) was added. Test #7 utilized the commercial product Q2-3225C made by Dow Corning as the polyoxyalkylene polysiloxane copolymer and cyclic silicone, which is believed to follow the teachings of U.S. Pat. Nos. 4,122,029 and 4,311,695 in a 90 wt. % water in cyclic tetramer emulsions. The preferred emulsion of this invention plus 0.5% Polymer JR ™ (test #3) gave very good wet and dry combability.

TABLE 2

| Test No. | Wet Combability | Dry Combability | Fly Away |
|---|---|---|---|
| 1 Control (H₂O) | 2.8 | 8.5 | 2.7 |
| 2 Preferred emulsion | 3.8 | 9.9 | 3.4 |
| 3 Preferred emulsion + 0.5% JR ™ | 10.0 | 9.4 | 6.6 |
| 4 Preferred emulsion + 0.5% LR ™ | 6.3 | 9.2 | 3.2 |
| 5 Preferred emulsion + 1% JR ™ | 6.0 | 7.0 | 4.2 |
| 6 Preferred emulsion + 1% LR ™ | 7.5 | 7.6 | 3.3 |
| 7 Q2-3225C | 5.0 | 9.8 | 3.4 |

In order to improve the performance of the preferred emulsion (91 wt parts water, 1.588 wt. parts preferred polyoxyalkylene polysiloxane and 7.412 wt. parts of the cyclic dimethylsiloxane tetramer) as a hair conditioner, a variety of additives which are listed in the CTFA Dictionary were evaluated. The additives that were oil soluble were added to the emulsifier concentrate. The water soluble components were added to the aqueous phase which then is added to the emulsifier concentrate. A wide variety of diverse personal-care components can be added without adversely effecting emulsion stability. Emulsions tested and results of the hair testing are given in Table 3 below, wherein the % of each listed additive is based upon the total weight of the final emulsion containing same.

TABLE 3

| Test No | Additives To Preferred Emulsion Composition | Wet Combability | Dry Combability | Fly Away |
|---|---|---|---|---|
| 1 | 1% dicetyl ammonium chloride, ½% POLYMER JR ™, 1% cetyl alcohol | 10 | 10 | 2.0 |
| 2 | ½% cetyl alcohol, ½% POLYMER JR ™ | 9.9 | 10 | 2.6 |
| 3 | ½% myristyl myristate | 7.1 | 10 | 2.0 |
| 4 | ½% myristyl myristate, 1% dicetyl ammonium chloride | 9.8 | 10 | 1.9 |
| 5 | ½% POLYMER JR ™, ½% myristyl myristate | 10 | 10 | 4.0 |
| 6 | 1% isopropyl myristate | 6.1 | 10 | 4.4 |
| 7 | ½% isopropyl linoleate | 7.1 | 9.9 | 4.5 |
| 8 | 1% cetyl alcohol | 3.4 | 10 | 1.5 |
| 9 | 1% dicetyl ammonium chloride | 4.8 | 9.1 | 2.1 |
| 10 | 1% glycerol monostearate, ½% POLYMER JR ™ | 3.0 | 10 | 1.5 |
| 11 | 1% dicetyl ammonium chloride, 1% cetyl alcohol | 7.4 | 10 | 1.5 |
| 12 | 1% Acetol 1706 ™ | 5.2 | 10 | 1.7 |
| 13 | 1% Ceteareth-20, ½% POLYMER JR ™ | 7.4 | 10 | 6.0 |
| 14 | ½% glycol monostearate, ½% POLYMER JR ™ | 5.8 | 10 | 4.2 |

TABLE 3-continued

| Test No | Additives To Preferred Emulsion Composition | Wet Combability | Dry Combability | Fly Away |
|---|---|---|---|---|
| 15 | 1% cetyl alcohol, ½% POLYMER JR ™ | 9.8 | 10 | 2.4 |
| 16 | 1% dicetyl ammonium chloride, ½% POLYMER JR ™ | 7.4 | 10 | 1.5 |
| 17 | 1% Acetol 1706 ™ ½% POLYMER JR ™ | 7.1 | 9.9 | 3.5 |
| 18 | ½% myristyl myristate, ½% stearamidopropyl dimethyl amine | 10 | 10 | 1.8 |
| 19 | 1% myristyl myristate | 9.2 | 10 | 3.7 |
| 20 | ½% myristyl myristate, ½% stearamidopropyl dimethyl amine, 0.2% POLYMER JR ™ | 10 | 10 | 1.7 |
| 21 | ½% stearamidopropyl dimethyl amine | 10 | 10 | 2.7 |
| 22 | ¼% myristyl myristate, ¼% stearamidopropyl dimethyl amine | 10 | 10 | 2.3 |

The data of Table 3 above demonstrate that the addition of a small amount, e.g. 1% or less, of certain additives dramatically improves the performance of the preferred emulsion of this invention as a hair conditioner. Myristyl myristate, in combination with stearamidopropyl dimethyl amine, are particularly effective even at concentrations as low as 0.25% each in improving the wet and dry combability and fly away resistance. These systems have even better combability and reduced fly away than the commercial hair conditioners tested above.

While the 90% water emulsions of this invention do not pass the freeze/thaw testing, they do have good stability at 50° C. The preferred emulsion composition as described above has good stability at 4° C. but the addition of certain types of emollients can cause low temperature instability. Presumably, at the lower temperatures the emollients are less soluble in the cyclic silicone and provide nucleation sites for the cyclic silicone which has a freezing point of 18° C.

Two additive emollients of considerable interest, myristyl myristate (C424) and stearamidopropyl dimethyl amine (S-13), were each tested alone in the preferred emulsion composition described above (91 wt. parts water, 1.588 wt. parts preferred polyoxyethylene polysiloxane, 7.412 wt. parts cyclic dimethyl siloxane tetramer) and were also tested with other modifiers to determine stability at 4° C. A particular emulsion is considered stable if it survives two weeks at 4° C. The various emulsions made pursuant to this study are identified in Table 4 below. The emulsions were prepared in the same manner as described above, i.e. the preferred emulsifier concentrate (see Example 1) in the amount of 30 wt. parts was placed into the bowl of the Hobart ™ mixer, mixed on the #1 setting of the Hobart ™ while adding water at the rate of 8.3 wt. parts per minute until a total of 270 wt. parts water were added over a period of 32.5 minutes. The temperature was controlled at 40° C. and after completion of water addition the heat was turned off and the emulsion was mixed for 10 additional minutes. Test series #1 included 0.5% of C-424 in the preferred emulsion with no other additives and resulted in a stable emulsion. In test series #2, 0.25% of each of the C-424 and S-13 were added and in the cases where no other additives were added and where 0.1% of Tergitol ™ 15-S-3 was added, the resulting emulsion was unstable. In the case where 0.16% Tergitol ™ 15-S-3, the case where 2% sodium chloride and the case where 0.2% Arlacel ™ 80 were also added, stable emulsions resulted. In test series #3, 0.5% of each of C-424 and S-13 were used in the emulsion. In the case where no other additives were added, no unstable emulsion resulted. In the case where 0.5% Arlacel ™ 80 was added, a stable emulsion resulted. In test series #4, 0.5% S-13 was added and no other additive.

TABLE 4

| | | Modifiers | | | | | |
|---|---|---|---|---|---|---|---|
| Test Series | % C-424:% S-13 | No Other Additives | 0.1% (1) TERGITOL ™ 15-S-3 | 0.16% (1) TERGITOL ™ 15-S-3 | 2% NaCl | 0.2% (2) Arlacel ™ 80 | 0.5% (2) Arlacel ™ 80 |
| 1 | 0.5:0 | S | — | — | — | — | — |
| 2 | 0.25:0.25 | U | U | S | S | S | — |
| 3 | 0.5:0.5 | U | — | — | — | — | S |
| 4 | 0:0.5 | U | — | — | — | — | — |

U = Unstable, S = Stable
(1) TERGITOL ™ 15-S-13 is a secondary alcohol ethoxylate containing an average of 3 moles of ethylene oxide with an HLB of 8.
(2) Arlacel ™ 80 is a Sorbitan oleate with an HLB of 4.3.

The emulsions indicated in Table 4 remained stable for at least one month at 4° C. after which time the tests were still continuing. The test results shown in Table 4 indicate that the addition of a small amount of a secondary organic surfactant improves the low temperature stability of emulsions which without additives are stable but when additives such as S-13 are added become unstable. The secondary organic surfactant presumably overcomes the low temperature destabilizing effect of S-13 by solubilizing it in the cyclic silicone tetramer. The preferred emulsion as identified above without additives is stable but when the S-13 is added, it becomes unstable whereupon the addition of a secondary organic surfactant improves the low temperature stability. Other organic surfactants that can be used in place of the above-identified Tergitol ™ 15-S-3 and Arlacel ™ 80 surfactants are well known and any suitable organic surfactant can be employed. For example, organic surfactants capable of preparing emulsions of the water-in-oil type and having a HLB value of 2 to 10 inclusive are useful. Such surfactants may be anionic, cationic or nonionic regarding its hydrophilic portion. Surfactants of this type include sodium capryl lactylate and sodium stearoyl lactylate as anionic surfactants, quaternary ammonium chlorides manufactured by Tomah Products, Inc. as Emulsifier Three ™ and Emulsifier Four ™ as a cationic surfactant and polyethylene glycol (200) monolaurate, glycerol monolaurate, N,N-dimethylcaproamide, diethylene glycol monolaurate, sorbitan monolaurate and nonylphenoxy polyethoxyethanol as non-ionic surfactants.

A wide variety of different kinds of personal-care components can be used in the novel personal-care emulsion compositions of this invention. Components soluble in the volatile silicone phase are hydrophobic materials such as polyvinylisobutyl ether waxes, such as cetyl alcohol and paraffin, and oils such as mineral oil, isopropyl myristate, non-volatile silicones and the like. The Examples provided herein set forth other useful personal-care components soluble in the volatile silicone phase.

Personal-care components that are water soluble include, but are not limited to, acrylamide, polyoxyethylene polymers, quaternary nitrogen polymers including quaternary nitrogen substituted hydroxyethyl cellulose ethers such as Polymer LR TM, Polymer JR TM and any of the hair conditioning agents set forth in U.S. Pat. No. 4,387,090 and British patent application No. 8218032, published 2/2/83 under #2102288A, and the quaternary substituted cellulose ethers disclosed in U.S. Pat. No. 3,472,840.

In addition, spermaceti wax, bees wax, lanolin wax, coconut oil, caster oil, lanolin oil, stearyl alcohol, lauryl alcohol, palmitic acid, stearic acid, methyl ethyl or isopropyl esters of fatty acids such as those listed above, petrolatum, perhydrosqualene can be used as personal care components. Also included as personal-care components are physiological components such as medicaments for treating skin conditions including chapped skin, athlete's foot and dermatitis and agents used for cleansing purposes. Other optical components can be added to the novel emulsion compositions of this invention including dyes, perfumes, opacifiers, pearlescent aids, buffers, preservatives, antioxidants, and antidandruff aids such as zinc pyrithione and sulfur.

EXAMPLE 1

An emulsifier concentrate was prepared by premixing for 15 minutes, 10 wt. parts water and 15.88 wt. parts of a polyoxyethylene substituted silicone having a molecular weight of 3120 and having the average formula:

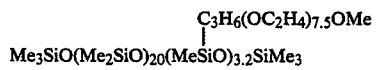

$$Me_3SiO(Me_2SiO)_{20}(MeSiO)_{3.2}SiMe_3$$
with a side chain $C_3H_6(OC_2H_4)_{7.5}OMe$ The mixing was carried out in a bench-top jar mill. Thereafter, 74.12 wt. parts of the cyclic tetramer of dimethylsiloxane, e.g. octamethyltetrasiloxane, was added and mixing was continued for 45 minutes. The resulting emulsifier concentrate was clear, colorless liquid having more than 90% light transmission as measured by a Brinkman colorimeter equipped with a fiber optic light guide and Pyrex flow-through probe. The resulting emulsifier concentrate had a specific gravity of 0.97, a flash point of 120° F. and a viscosity of 35 centistokes at 25° C.

EXAMPLE 2A

A hair conditioning formulation exhibiting excellent wet and dry combability and minimal fly away was prepared from the following materials. Parts A, B and C given below in Table 5A were each prepared separately by mixing ingredients listed in each Part.

TABLE 5A

| Part | Ingredient | Wt. % |
|---|---|---|
| A | Emulsifier concentrate of Example 1 | 10.0 |
|   | Myristyl myristate (1) | 0.5 |
|   | Stearamidopropyl dimethyl amine (2) | 0.5 |
|   | Sorbitan oleate, HLB of 4.3 (3) | 0.2 |
| B | Sodium chloride | 0.2 |
|   | Deionized water | 87.6 |
| C | Diazolidinyl urea (preservative) (4) | 1.0 |
|   | Perfume | q.s. |

(1) Ceraphyl TM 424, Van Dyk
(2) Lexamide TM S-13, Inolex
(3) Arlacel TM 80, ICI
(4) Germall TM II, Sutton Industries
*Sufficient quantity Thereafter, Parts A and B were separately heated to 40° C. and Part B was added to Part A slowly with good mixing under moderate shear. Mixing was continued and the mixture was cooled to 30° C. Thereafter, Part C was added and the resulting mixture was mixed and cooled to 25° C. The resulting hair conditioner formulation provided excellent wet and dry combability and minimal fly away characteristics. The resulting hair conditioner formulation also had good stability at 4° C. and 50° C.

EXAMPLE 2B

A hair conditioning formulation was prepared from the following materials. Parts A, B and C given below in Table 5B were each prepared separately by mixing ingredients in each Part.

TABLE 5B

| Part | Ingredient | Wt. % |
|---|---|---|
| A | Q2-3225C | 10.0 |
|   | Myristyl myristate | 0.5 |
|   | Stearamidopropyl dimethyl amine | 0.5 |
|   | Sorbitan oleate | 0.2 |
| B | Sodium chloride | 0.2 |
|   | Deionized water | 87.6 |
| C | Diazolidinyl urea | 1.0 |
|   | Perfume | q.s. |

Thereafter, Parts A and B were separately heated to 40° C. and Part B was added to Part A slowly with good mixing under moderate shear. Mixing was continued and the mixture was cooled to 30° C. Thereafter, Part C was added and the resulting mixture was mixed and cooled to 25° C. The resulting hair conditioner formulation was extremely thick almost to the point of being nonpourable. On standing overnight, the emulsion separated into two layers with both layers being inhomogeneous.

EXAMPLE 3

A light moisturizing cream formulation was prepared in this example. Each of Parts A, B and C were separately prepared by mixing the ingredients listed below in Table 6 for each Part.

TABLE 6

| Part | Ingredient | Wt. % |
|---|---|---|
| A | Emulsifier concentrate of Example 1 | 30 |
|   | Stearic acid | 5 |
|   | Myristyl myristate | 2.0 |

TABLE 6-continued

| Part | Ingredient | Wt. % |
| --- | --- | --- |
| B | Glycerol | 1.0 |
| | Propylene glycol | 1.0 |
| | 1 wt. % aqueous solution of quaternary nitrogen substituted cellulosic ether (5) | 60.0 |
| C | Diazolidinyl urea (preservative) | 1.0 |
| | Perfume | q.s. |

(5) Polymer LR-400 ™, Union Carbide Corporation

Parts A and B were separately prepared and each Part was heated to 55° C. Thereafter, Part B was added slowly to Part A with good mixing under moderate shear. Mixing was continued and the mixture was allowed to cool to 40° C. Thereafter, Part C was mixed into the mixture of Parts A and B and the resulting mixture of all three Parts was mixed and cooled to 25° C. The resulting formulation was a white, low viscosity, fine cream, adapted especially for use as an under-makeup moisturizer or for use in the absence of makeup. This cream is also excellent for body application. The resulting cream had good stability at 50° C. and 4° C. and was capable of surviving five freeze/thaw cycles as a result of the relatively lower level of water.

EXAMPLE 4

A hand and body lotion formulation was prepared from each of Parts A, B and C identified in Table 7 below.

TABLE 7

| Part | Ingredient | Wt. % |
| --- | --- | --- |
| A | Emulsifier Concentrate of Example 1 | 15 |
| | Stearic acid | 2.75 |
| | Butyl stearate | 1.5 |
| | Stearyl stearate | 0.5 |
| | Glycerol monostearate SE | 0.25 |
| B | 2 wt. % aqueous solution of CMC-cellulose gum (6) | 79 |
| C | Diazolidinyl urea | 1.0 |
| | Perfume | q.s. |

(6) Hercules

Parts A and B were separately prepared and then heated separately to 55° C. Part B was then slowly added to Part B with good mixing under moderate shear. Mixing was continued and the resulting mixture was cooled to 40° C. Thereafter, Part C was mixed into the mixture of Parts A and B and the resulting mixture was mixed and cooled to 25° C. There resulted a non-ionic, medium viscosity, white lotion having a soft, silky, non-greasy afterfeel. This lotion had good stability at 50° C. and 4° C. and was able to survive five freeze/thaw cycles.

EXAMPLE 5

A night cream was prepared from Parts A, B and C listed in Table 8 below:

TABLE 8

| Part | Ingredient | Wt. % |
| --- | --- | --- |
| A | Emulsifier concentrate of Example 1 | 30.0 |
| | Stearic acid | 3.5 |
| | Stearyl stearate | 2.0 |
| | Glycerol monostearate SE | 0.5 |
| B | 1% aqueous solution of quaternary nitrogen substituted cellulosic ether (5) | 63.0 |
| C | Diazolidinyl urea | 1.0 |
| | Perfume | q.s. |

Parts A and B were separately prepared and separately heated to 55° C. Thereafter, Part B was slowly added to Part A with good mixing under moderate shear. Mixing of the mixture was continued and it was cooled to 40° C. Then Part C was mixed into the mixture of Parts A and B and the resulting mixture was cooled to 25° C. There was obtained a glossy, soft cream which was useful for overnight skin conditioning. The resulting night cream had good stability at 50° C. and 4° C. and was capable of surviving five freeze/thaw cycles.

EXAMPLE 6

An anti-perspirant formulation was made by heating slowly with stirring 40 wt. % of a 50 wt. % aqueous solution of aluminum chlorohydrate and 60 wt. % of the emulsifier concentrate prepared in the manner described in Example 1. A translucent mixture was formed which separated into two layers which are very readily redispersed with mild agitation. The resulting anti-perspirant composition would have good stability at 50° C. and 4° C.

EXAMPLE 7

A sunscreen cream formulation was prepared in this example. Each of Parts A, B and C were separately prepared by mixing the ingredients listed below in Table 9 for each Part.

TABLE 9

| Part | Ingredient | Wt. % |
| --- | --- | --- |
| A | Emulsifier concentrate of Example 1 | 28 |
| | Octyl para-dimethylamino-benzoate (sunscreen) | 2 |
| | Stearic acid | 5 |
| | Myristyl myristate | 2.0 |
| B | Glycerol | 1.0 |
| | Propylene glycol | 1.0 |
| | 1 wt. % aqueous solution of quaternary nitrogen substituted cellulosic ether (5) | 60.0 |
| C | Diazolidinyl urea (preservative) | 1.0 |
| | Perfume | q.s. |

(5) Polymer LR-400 ™, Union Carbide Corporation

Parts A and B were separately prepared and each Part was heated to 55° C. Thereafter, Part B was added slowly to Part A with good mixing under moderate shear. Mixing was continued and the mixture was allowed to cool to 40° C. Thereafter, Part C was mixed into the mixture of Parts A and B and the resulting mixture of all three Parts was mixed and cooled to 25° C. The resulting formulation was a white, low viscosity, fine cream, adapted especially for use as suntan cream and moisturizer. The resulting cream had good stability at 50° C. and 4° C. and was capable of surviving five freeze/thaw cycles as a result of the relatively lower level of water.

EXAMPLE 8

An emulsifier concentrate was prepared by premixing for 15 minutes, 10 wt. parts water and 15.88 wt. parts of a polyoxyethylene substituted silicone having a molecular weight of 3120 and having the average formula:

$$\underset{|}{\text{Me}_3\text{SiO}(\text{Me}_2\text{SiO})_{20}(\text{MeSiO})_{3.2}\text{SiMe}_3}\overset{\text{C}_3\text{H}_6(\text{OC}_2\text{H}_4)_{7.5}\text{OMe}}{}$$

The mixture was carried out in a bench-top jar mill. Thereafter, 74.12 wt. parts of the cyclic dimethylsiloxane pentamer, e.g., decamethylpentasiloxane, was added and mixing was continued for 45 minutes. The resulting mixture was clear, colorless liquid having more than 90% light transmission.

EXAMPLE 9

A night cream was prepared from Parts A, B and C listed in Table 10 below:

TABLE 10

| Part | Ingredient | Wt. % |
|---|---|---|
| A | Emulsifier concentrate of Example 8 | 30.0 |
|   | Stearic acid | 3.5 |
|   | Stearyl stearate | 2.0 |
|   | Glycerol monostearate SE | 0.5 |
| B | 1% aqueous solution of quaternary nitrogen substituted cellulosic ether (5) | 63.0 |
| C | Diazolidinyl urea | 1.0 |
|   | Perfume | q.s. |

Parts A and B were separately prepared and separately heated to 55° C. Thereafter, Part B was slowly added to Part A with good mixing under moderate shear. Mixing of the mixture was continued and it was cooled to 40° C. Then Part C was mixed into the mixture of Parts A and B and the resulting mixture was cooled to 25° C. There was obtained a glossy, soft cream which was useful for overnight skin conditioning. The resulting night cream would have good stability at 50° C. and 4° C. and would be capable of surviving five freeze/thaw cycles.

What is claimed is:

1. Water-in-silicone personal care emulsion comprising
(a) 25 to 98 wt. % water,
(b) 1.6 to 75 wt. % of a volatile cyclic silicone liquid having a normal boiling point of less than 250° C. and having the formula:

$$[R_2SiO]_x$$

wherein R is alkyl having 1 to 4 carbon atoms and x is an integer of 4 to 6;
(c) 0.1 to 30 wt. % of a personal-care component; and
(d) 0.3 to 5 wt. % of a polyoxyalkylene substituted silicone having the average formula: $MD_yD°_zM$, wherein M is a trialkylsiloxy unit having the average formula $R_3SiO_{0.5}$, D is a dialkylsiloxy unit of the formula $R_2SiO$, D° is a polyoxyalkylene substituted alkylsiloxy unit of the average formula:

$$\underset{|}{\text{RSiO}}\overset{\text{C}_n\text{H}_{2n}(\text{OC}_b\text{H}_{2b})_a\text{OR}°,}{}$$

R is an alkyl group having 1 to 4 carbon atoms, R° is a terminal group selected from the group consisting of, alkyl, aryl, aralkyl and acyl radicals, n is an integer of 2 to 8, a is a number of 5 to 12, b is 2, y is a number of 5 to 100 in which the polyoxyalkylene group has a molecular weight of less than 1000, z is a number of 1 to 16, said percentages being based on the total weight of (a), (b), (c) and (d).

2. Water-in-silicone personal care emulsion as claimed in claim 1 wherein the polyoxyalkylene chain $(OC_bH_{2b})_a$ of said polyoxyalkylene substituted silicone contains an average of at least 50 wt. % polyoxyethylene units.

3. Water-in-silicone personal care emulsion as claimed in claim 1 wherein said personal care component is soluble in the cyclic silicone phase.

4. Water-in-silicone personal care emulsion as claimed in claim 1 wherein said personal care component is soluble in the aqueous phase.

5. Water-in-silicone personal care emulsion as claimed in claim 1 wherein said emulsion contains two or more personal care components at least one of which is soluble in the aqueous phase and at least another one of which is soluble in the cyclic silicone phase.

6. Water-in-silicone personal care emulsion as claimed in claim 9 wherein said personal care component is selected from the group consisting of ester waxes, oils and fats of animal or vegetable origin, fatty alcohols, fatty acids, alkyl esters of fatty acids, hydrocarbon oil and waxes, glycerol esters of fatty acids, CMC cellulose gums, quaternary N-substituted cellulose ethers, aliphatic polyols, and fatty acid amidoalkyl dialkyl amines.

7. Water-in-silicone personal care emulsion as claimed in claim 1 wherein the amount of water is 60 to 90 wt. %, the amount of volatile cyclic silicone liquid is 5 to 40 wt. %, the amount of personal care component is 1 to 25 wt. % and the amount of polyoxyalkylene substituted silicone is 1 to 5 wt. %.

8. Water-in-silicone personal care emulsion as claimed in claim 7 wherein said cyclic silicone liquid is $[Me_2SiO]_4$ and said polyoxyalkylene substituted silicone has the average formula:

$$\underset{|}{\text{Me}_3\text{SiO}(\text{Me}_2\text{SiO})_y(\text{MeSiO})_z\text{SiMe}_3}\overset{\text{C}_3\text{H}_6(\text{OC}_b\text{H}_{2b})_a\text{OMe}}{}$$

wherein y, z, b and a are as defined in claim 9.

9. Water-in-silicone personal care emulsion as claimed in claim 8 wherein said polyoxyalkylene substituted silicone has the average formula:

$$\underset{|}{\text{Me}_3\text{SiO}(\text{Me}_2\text{SiO})_{20}(\text{MeSiO})_{3.2}\text{SiMe}_3}\overset{\text{C}_3\text{H}_6(\text{OC}_2\text{H}_4)_{7.5}\text{OMe}}{}$$

10. Water-in-silicone emulsion hair conditioner as claimed in claim 17 wherein the amount of water is 75 to 98%, the amount of cyclic silicone is 1 to 20 wt. %, the amount of personal care component is 0.5 to 3 wt. %, and the amount of polyoxyalkylene substituted silicone is 0.5 to 2%.

11. Water-in-silicone emulsion hair conditioner as claimed in claim 10 wherein said personal care components include myristyl myristate, stearamidopropyl dimethyl amine and sorbitan oleate.

12. Water-in-silicone emulsion moisturizing cream as claimed in claim 9 wherein the amount of water is 50 to 75 wt. %, the amount of cyclic silicone is 15 to 35 wt. %, the amount of personal care component is 5 to 15 wt. % and the amount of polyoxyalkylene substituted silicone is 2 to 10 wt. %.

13. Water-in-silicone emulsion moisturizing cream as claimed in claim 12 wherein said personal care component includes stearic acid, myristyl myristate, glycerol, propylene glycol and a quaternized hydroxyethyl cellulose ether.

14. Water-in-silicone emulsion night cream as claimed in claim 9 wherein the amount of water is 50 to 75 wt. %, the amount of cyclic silicone is 15 to 35 wt. %, the amount of personal care component is 5 to 15 wt. % and the amount of polyoxyalkylene substituted silicone is 2 to 10 wt. %.

15. Water-in-silicone emulsion night cream as claimed in claim 14 wherein said personal care component includes stearic acid, stearyl stearate, glycerol monostearate and a quaternized hydroxyethyl cellulose ether.

16. Water-in-silicone emulsion hand and body lotion as claimed in claim 9 wherein the amount of water is 70 to 85 wt. %, the amount of cyclic silicone is 5 to 15 wt. %, the amount of personal care component is 5 to 15 wt. % and the amount of polyoxyalkylene substituted silicone is 1 to 15%.

17. Water-in-silicone emulsion hand and body lotion as claimed in claim 16 wherein said personal care component includes stearic acid, butyl stearate, stearyl stearate, glycerol monostearate and a carboxyl methyl cellulose gum.

18. Water-in-silicone emulsion anti-perspirant formulation as claimed in claim 9 wherein said personal care component is aluminum chlorohydrate, the amount of water is 20 to 30 wt. %, the amount of cyclic silicone liquid is 40 to 50 wt. %, the amount of aluminum chlorohydrate is 15 to 25 wt. % and the amount of polyoxyalkylene substituted silicone is 5 to 25 wt. %.

19. Water-in-silicone personal care emulsion as claimed in claim 7 wherein said cyclic silicone liquid is [Me$_2$SiO]$_5$ and said polyoxyalkylene substituted silicone has the average formula:

20. Water-in-silicone emulsion night cream as claimed in claim 19 wherein the amount of water is 50 to 75 wt. %, the amount of cyclic silicone is 15 to 35 wt. %, the amount of personal care component is 5 to 15 wt. % and the amount of polyoxyalkylene substituted silicone is 2 to 10 wt. %.

21. Water-in-silicone emulsion night cream as claimed in claim 20 wherein said personal-care component includes stearic acid, stearyl stearate, glycerol monostearate and a quaternized hydroxyethyl cellulose ether.

* * * * *

UNITED STATES PATENT AND TRADEMARK OFFICE
CERTIFICATE OF CORRECTION

PATENT NO. : 4,801,447
DATED : January 31, 1989
INVENTOR(S) : Mary L. Gum

It is certified that error appears in the above-identified patent and that said Letters Patent is hereby corrected as shown below:

Column 6, line 26, "lane" should read --lene polysiloxane--.

Column 7, line 53, "present" should read --presented--.

Column 8, line 21, "wt" should read --wt.--.

Column 8, line 39, "No" should read --No.--.

Column 9, line 60, "(C424)" should read --(C-424)--.

Column 10, line 22, "no" should read --an--.

Column 16, lines 31 and 54 the numeral "9" should read --1--.

Column 16, line 64, the numeral "17" should read --9--.

Signed and Sealed this

Fifth Day of December, 1989

*Attest:*

JEFFREY M. SAMUELS

*Attesting Officer*   *Acting Commissioner of Patents and Trademarks*